(12) United States Patent
Sferco

(10) Patent No.: US 6,899,721 B2
(45) Date of Patent: May 31, 2005

(54) INSTRUMENT FOR PERFORMING SURGICAL CHOLANGIOGRAPHY

(76) Inventor: Ruben Juan Sferco, Lafinur 4050, Barrio Urca 5009, Córdoba (AR)

( * ) Notice: Subject to any disclaimer, the term of this patent is extended or adjusted under 35 U.S.C. 154(b) by 586 days.

(21) Appl. No.: 10/125,343

(22) Filed: Apr. 19, 2002

(65) Prior Publication Data

US 2003/0018249 A1 Jan. 23, 2003

(30) Foreign Application Priority Data

Apr. 26, 2001 (AR) ........................................ P010101951

(51) Int. Cl.[7] .............................................. A61B 17/28
(52) U.S. Cl. ........................ 606/205; 606/207; 600/420
(58) Field of Search ................................ 606/205–207; 600/419–420

(56) References Cited

U.S. PATENT DOCUMENTS

| | | |
|---|---|---|
| 5,071,412 A | 12/1991 | Noda |
| 5,147,334 A | 9/1992 | Moss |
| 5,176,647 A | 1/1993 | Knoepfler |
| 5,183,470 A | 2/1993 | Wettermann |
| 5,224,931 A | 7/1993 | Kumar |
| 5,236,417 A | 8/1993 | Wallis |
| 5,269,754 A | 12/1993 | Rydell |
| 5,350,384 A | 9/1994 | Clement et al. |
| 5,496,310 A | 3/1996 | Exconde et al. |
| 5,626,607 A * | 5/1997 | Malecki et al. ............. 606/205 |
| 5,855,590 A * | 1/1999 | Malecki et al. ............. 606/205 |
| 5,895,361 A * | 4/1999 | Turturro ..................... 600/562 |
| 6,368,340 B2 * | 4/2002 | Malecki et al. ............. 606/204 |

* cited by examiner

Primary Examiner—(Jackie) Tan-Uyen T. Ho
(74) Attorney, Agent, or Firm—Crowell & Moring LLP

(57) ABSTRACT

An instrument for performing surgical cholangiography during either conventional colecistectomy or video-laparoscopic cholecistectomy included a tube slidably mounted into another having a rotative bidigital control. The control allows sliding such that the outer tube ending to acts on a forceps at the inner tube ending, making the forceps jaws move away or come near each other, causing the jaws to respectively move away or approach a needle, which also belongs to the inner tube, is centered between the jaws, and is used for cannulating the cystic duct. The jaws, in closed function when the needle is in the duct, press the duct and needle together, avoiding both sliding of the needle and escape of the contrast liquid which is injected from the other end of the inner tube. During the video-laparoscopic cholecistectomy, the design and size of the instrument allow it to enter the abdominal cavity through a cannula with a diameter less than others commonly used in this type of surgery.

9 Claims, 3 Drawing Sheets

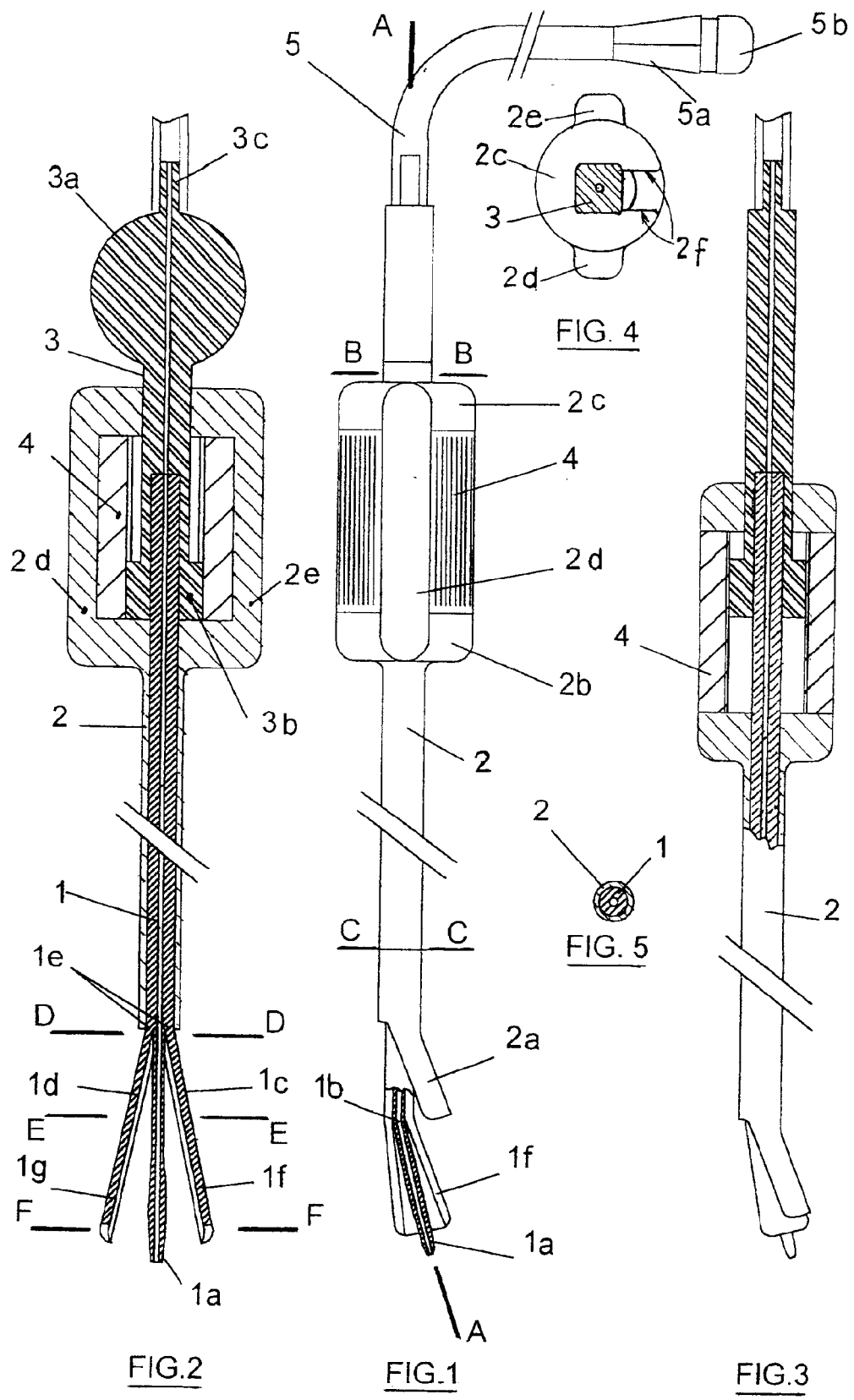

INSTRUMENT FOR PERFORMING SURGICAL CHOLANGIOGRAPHY

The benefit of the filing date of prior Argentinean application P 01 01 01951, filed Apr. 26, 2001, is hereby claimed, and the entire disclosure of this prior Argentinean application is incorporated herein by reference.

Surgical cholangiography is the method for performing a radiography of bile ducts when gallbladder removal is carried out during a surgical procedure. It is necessary that ducts be previously filled with a radiopaque medium, which stop X-rays. Thereby when the radiography is carried out, we can see the image of the contrast medium in the ducts and so, it is possible to know their inner diameters, their length, their paths and if they have either any stones or any tumors therein.

FIELD OF INVENTION

This instrument is very important for medical surgical investigation of gallbladder, cystic duct and main biliar ducts so as to know if they have any abnormalities and then which treatment is more convenient to perform. The device can be used either during conventional cholecystectomy making a large opening of the body cavity or during the laparoscopyc cholecystectomy making several micro incisions which allow the insertion of several surgery instruments and a small video camera connected to a video monitor, providing a picture of the organs in the abdominal cavity. Laparoscopic cholecystectomy began twenty years ago and today is the preferred surgical technique because it allows a less painful recovery, shorter-term hospitalization, both faster and better aesthetic formation of scars; patients can return to work in 7 to 10 days. The biggest advantages of the present instrument are observed during the performance of the laparoscopic cholecistectomy; therefore the following description is using this device during laparoscopic cholecistectomy.

BACKGROUND OF THE INVENTION AND PROBLEMS WHICH NEED TO BE SOLVED

Laparoscopic gallbladder surgery is very much known to the biliary surgery specialist, in such a way that the description of this technique will not be expressed but it is necessary to say that four micro incisions on the upper part of the abdomen in accordance with biliary topography are made in places, which for carrying out the surgical steps better are known as the most convenient. In the micro incisions and through the abdominal wall some 5 mm. to 10 mm. diameter size cannulae are placed and, through them a variety of instruments are introduced which the surgeon manipulates from outside the patient's body, being guided by looking at images on a monitor transmitted from the abdominal cavity by a video camera inserted into the abdominal cavity.

For performing surgical cholangiography it is necessary to follow some surgical steps, which at present are quite similarly regulated in most surgical centers. In short they are:

1-Surgical search of the cystic duct.
2-Dissection of cystic duct for its perfect identification.
3-Putting either a ligation or clamping or clipping the cystic duct near the gallbladder neck.
4-Placing the cystic duct in tension by grasp-and-traction of gallbladder with suitable instruments.
5-Making a cross micro incision in the cystic duct thereby reaching its inner diameter through a small opening it is possible to enter into the cystic duct.
6-Inserting either a blunt tip rigid needle or a flexible catheter in the cystic duct opening which allows the injection of a radiopaque medium.
7-Ligation, clamping or clipping the cystic duct very closely to the cystic opening embracing the needle or catheter already introduced in it, thereby avoiding their displacement or escape of injected liquid outside the duct, thereby causing a dark spot in the biliary duct region for X-rays.
8-Injection of a radiopaque medium.
9-Taking the X-rays.
10-Extraction of the ligation, clamp or clip, which is pressing both the duct and needle or catheter.
11-Extraction of needle or catheter. This is the last step of the cholangiography.

The instrument we are speaking about takes part in steps numbered 6, 7, 8, and 10, therefore, with reference to the execution of these steps, the present state of the technique and its disadvantages will be described.

Step 6 is carried out introducing the catheter or needle into the abdominal cavity through one of the cannulae which have been placed during previous steps; therefore it is necessary first to extract the instrument which had been inserted in it. Another way is using a new cannula, which is situated in an abdominal place that allows the catheter or needle to be more easily oriented toward the cystic duct opening. A catheter is very difficult to insert in the cystic duct opening except if the duct inner diameter is dilated. This fact and other causes, which are unnecessary to mention now, make the use of catheters rare. Mostly the duct diameter is decreased, normal or little dilated and then the employing of a needle makes the procedure easier. However, using a cannula, placed during previous steps, the abdominal place where it was placed makes this step very difficult to carry out because it is not possible to get a needle-duct wide-incidence angle so that the needle and duct be almost parallel with each other. This is very important for allowing the needle tip inserted in the cystic duct opening, to slide 5 to 10 mm. into the duct without endangering the diametrically opposite wall. This problem is minimized putting a new cannula such as mentioned above but; even so employing the normal straight needle, this step is not easy, it is slow and the risk for injuring the duct wall is present.

Step 7 is carried out putting a metal clip using a suitable forceps: an instrument inserted in a cannula is brought out and, through this cannula the forceps carrying the clip between its jaws is introduced into the abdominal cavity. For easier understanding, we can say the clip is the same as a small, metallic U letter. Clips were made for shutting some vein or artery off completely by strongly driving the forceps handles and reaching the end of its running. In such a way, both arms of the clip being around the vessel, it is completely flattened. Going back to step 7, we have to remember it is necessary for avoiding both the needle to slide and the injected radiopaque medium to escape outside the duct. The clip is carried on the forceps so that the cystic duct remains between its parallel arms, and then with his skilful hand the surgeon operates the forceps with very controlled movements and force in such a way that the cystic duct walls are sufficiently pressed against the needle to avoid both the sliding of the needle and the escaping of some liquid; but not so much as to making the clip extraction difficult. The clip-applying forceps has not been designed for being used in this way; therefore, step 7 will be effective in accordance with both experience and ability of the surgeon, as well as the tactile and pressing sensibility of his hand and also according to the functional state of the forceps. This is a resterilizeable metallic several-joint instrument and after each surgical operation must be washed and lubricated and then sterilized. Sometimes this procedure is not perfectly carried out and the forceps joints get hard and then it is possible for the surgeon to have a wrong appraisal of how much pressure is reached on the arms of the clip. These facts cause step 7 not to be absolutely trusted and therefore it is necessary to control if the clip correctly presses the needle. For this control the surgeon gradually slackens the pressure of the forceps on the clip; at the same time with his other hand he slightly attempts the needle to slide, holding the clip and forceps relative position so as to press with higher force if the clip is slack and then repeating the procedure. All of this obviously prolongs the surgical time. For carrying out step 8 a flex catheter connected with the needle on one of its endings and with a syringe on its second ending is employed. Saline liquid is injected watching if it escapes outside of the duct. If this happens we must change the clip for getting a better occlusion of the duct and then it is necessary to vacate some other cannula and through it a forceps slides for making traction of the clip. The forceps carrying the clip is brought out of the abdominal cavity and then, now carrying a new clip, the forceps is introduced to press the clip around the cystic duct. The clip is controlled in accordance to step 7 and again the saline liquid injection is made for controlling whether the liquid escapes or not and, if this is OK, the contrast medium is finally injected. Although the clip has been correctly mounted, the increased pressure of the liquid while it is injected into the cystic duct could cause the liquid to escape. This happens when the needle fits the cystic duct loosely: the parallel arms of the clip press the duct walls against the needle without surrounding them but the arms remain parallel in such a way that duct section walls at the clip zone are partially separate having a free communication between the lumen duct and outside through the duct opening.

Step 10 is the clip extraction and it is carried out getting a forceps into the abdominal cavity which catches the clip handle and by traction separates it from the duct, being, together with the forceps, carried outside. If the clip is slackly mounted its extraction in general is not difficult but, when it is strongly pressed it is necessary to traction strongly and, it is possible, at times that the clip and the cystic duct are separated; the forceps makes an uncontrolled movement which following both direction and sense of the traction are able to injure nearby organs. Whether the clip was slack or not, it is sometimes possible, along the extraction way, for the clip to fall in the abdominal cavity, being necessary to catch it again and get it outside; but if the clip is covered by bowels, then it will not be easy to find it, however the surgeon must look for it and get it outside to avoid future injuries of organs.

Several devices and instruments for overcoming the above said difficulties have been thought up. One of them does not employ the clip for fastening the cystic duct and needle, a forceps is employed, which directly presses the duct and needle getting a correct fix of them and an easy extraction of the forceps, but the forceps being radiopaque can obscure visibility of the biliary duct region for X-rays if the forceps remains between the X-rays and the biliary duct region. Sometimes this fact happens, then it is necessary to change the forceps position and the X-rays study must be repeated, meaning waste of time.

Kumar noted that reasons for the high failure rate of the cystic duct cannulation may be attributed to the narrow and tortuous anatomic structure of this duct and in 1993 he presents (U.S. Pat. No. 5,224,931) an instrument having a forceps and a side channel for introduction of a catheter, which is inserted in the gallbladder infindibulum (also known as pouch of Harmann). Medical reasons disqualify as a first election the option of cannulating the infundibulum instead of the cystic duct. In 1994 Clement et al. (U.S. Pat. No. 5,350,384) presented an instrument which also combines a forceps and a side channel for introduction of a catheter, which for inserting into the cystic duct must be obliquely deflected and, this act as also both the flexibility of the catheter and the anatomic cystic duct characteristic (the valves, the narrowness and the tortuousness of its inner diameter) sometimes make the catheter sliding difficult In 1996 Exconde et al. (U.S. Pat. No. 5,496,310) presented an instrument for performing cholangiographys through the cystic duct but it had a complicated design and low advantages. These inventions and others also patented do not overcome the whole afore mentioned difficulties in the surgical steps. Every one of them being a metallic instrument has a jaw mechanism which is driven through many joints and because of the high cost they do not have to be discarded so, they must be resterilized and this act makes them functionally less safe.

One object of this invention is to provide a suitable instrument for performing surgical cholangiography associated with either conventional or laparoscopic cholecistectomy and also allowing for the reduction of time at present required for this surgical procedure.

Another object is to provide an instrument, which reduces the risk for opening the cystic duct during cannulation by the needle.

Another object is to provide an instrument which allows the needle introduced in the cystic duct to remains fastened avoiding its sliding and besides avoiding the injected liquid to escape outside the duct.

Another object is to provide a safe instrument which allows injecting the contrast liquid directly being unnecessary to previously control escapes using the injection of saline liquid.

Another object is to provide an instrument which allows an easy extraction of the needle fastening without the risk of injuring nearby organs because of uncontrolled movements.

Another object is to provide an instrument with a simple design, without many joints and easy handling and whose effectiveness does not depend on previous surgeon experience.

Another object is to provide an instrument which allows to be driven from outside the body, is introduced in the abdominal cavity through a very flexible, small diameter and thin cannula that is inserted together with a conventional trocar crossing the abdominal wall.

Another object is to provide an instrument whose design allows low cost construction and together with both the cannula and the trocar constitute a non-resterilizable kit.

BRIEF DESCRIPTION OF THE INVENTION

The present invention comprises an assembly formed by a long and narrow first tube which is slidably mounted in a second tube. Both endings of the first tube are free endings because they are not covered by the second tube because the said endings surpass the endings of the second tube. For performing laparoscopic cholecistectomy, besides of the said assembly it is necessary to add a cannula with a mating trocar.

Thereby this assembly presents:

A far free ending of the first tube.

A first tube body extended along between both second tube endings and wholly covered by it.

A near free ending of the first tube.
A second tube.
A cannula and its trocar.

1-The far free ending of the first tube is the needle of the instrument and has an outer diameter smaller than the first tube body diameter and both diameters are concentric diameters, therefore they have a common axis. The needle has a gentle elbow near half of its length and a 15 degree angle is formed between the axis of the last segment of said elbow and said common axis. The diameter of this last segment gradually increases reaching a maximum and then it gradually decreases for reaching the initial diameter on the tip; thereby the last segment has an olive form.

2-The first tube body diameter is regular along the whole length, and on the body end, which is united to the needle, and diametrically opposed at both side of the needle, there are the birth points of respective and symmetric projections. These projections are contained in a common plane with the needle and at both sides of it, they advance in a divergent form in such a way that the needle remains centered in the common axis and each projection axis determines with said common axis a 15 degree angle. The projections reach a length of around 2-mm. less than the needle length. The said common plane is at right angles with the plane which contains the 15 degree angle of said needle last segment. Each projection has an elbowed last segment at an angle which is in all similar to the needle angle; thereby if both projections are pressed toward the mid line, they turn around the respective said birth points, being able to contact each other and the needle remaining placed between them, and so, the needle axis becomes the central axis of both projections along the whole lengths. When the pressing against both projections is suppressed, the 30 degree angle that had been separating the projections is recovered because both projections have enough memory or elasticity. Both projections behave the same as a forceps and each said elbowed last segment forms one of the forceps jaws. The jaw faces which contact each other present non-skid surfaces. On the afore mentioned birth points, the section of each projection is like a half crown confronting each concavity with each other having its bigger radio the same size as the said first tube outer radio and being its smaller radio the same as the needle outer radio and the center of said radios being placed on said common axis.

This section is not modified until the elbow; from right here both radios gradually increase whereby the following sections are not like a half crown but sectors of a crown because along the whole projection length the arrows have the same magnitude as the radio of the birth-point section. Also the chord gradually increases, whereby on each projection tip, the chord of the bigger radio is one time and a half bigger than the first tube diameter.

3-The near free ending of the first tube is the continuation of the first tube body and along its whole length is fixedly lodged into a tubular member whose inner section is circular in accordance with the diameter and length of the free near ending of the first tube and whose outer section is square, being a length bigger than the circular inner section length. On the distal ending of the square outer section a small segment has a circular shape, its diameter is bigger than the square diagonal and, this small segment is threaded on its whole length. Forming part of a handle and on its near ending, this tubular member becomes a disc with two plane faces, which are a circularly expanded continuation of two opposite faces of the square section, being parallel with each other and with said common axis that is centered between the two planes. A hole centered on this common axis diametrically crosses this disc and following along the tubular member it reaches the first tube. From the opposed ending a short tubular appendix belonging to the handle the hole continues. A low memory flex tube whose free ending has a female cone adapted for a standard syringe with a conventional plug is welded on the appendix. A rotative button with bidigital control, being a cylinder of annular section is mounted on the threaded segment of the tubular member.

There is a 0.5 mm. diameter hole along the whole length of the first tube longitudinal axis. Both mentioned endings and the first tube body are a single piece. For a better understanding they were described in a separate way.

4-Both inner and outer diameters of the second tube are regular along its approximately 160 mm. length. This tube has two endings:

The second tube ending proximate to the distal free ending of the first tube can slide and, advancing on said first tube body projections makes said jaws gradually approach each other. The second tube ending has an oblique opening and an elbowed small last segment at a 15-degree angle with said common axis. This angle is contained in the same plane that contains the needle elbow angle and mates with the convex angle determined by the jaws when the second tube being wholly slid makes the jaws contact These both elbowed last segment and oblique opening determine bigger press force of the jaws.

The second tube opposite ending has a small last segment whose outer diameter is increased looking like a ring but its inner diameter is the continuity of the second tube inner diameter. The ring has two diametrically opposed projections of a rectangular section being parallel both with each other and with said common axis and being contained by a plane normal to the plane where the angle of the said elbowed small last segment is contained. The projections are backward extending so as to reach another ring with the same outer diameter and height as the foresaid ring but its inner section is a square for allowing longitudinal sliding of the tubular member of the handle. One side of the square is outward opened along its whole height looking like a slot that is limited by planes which are both parallel with each other and normal to said side. The slot width is slightly less than the square side of the tubular member but, for allowing the tubular member to be mounted, the ring yields elastically and going back to its previous state blocks the tubular member so it can not have any side movement. The diameter and separation of both rings are similar to the diameter and length of the said rotative button respectively.

Said ring, said projection and said second tube are a single piece.

5-The cannula and its trocar are conventional ones and do not form part of the present invention.

BRIEF DESCRIPTION OF THE DRAWING

For a better understanding of the present instrument, a particular embodiment making reference to the enclosed drawings will be described which shows the essential parts of the invention schematically. The drawings are:

FIG. 1 is a view of the instrument in the separated jaws function with a partially cross-sectional view of the far ending.

FIG. 2 is a cross-sectional view of FIG. 1 taken along line AA.

FIG. 3 is a view of the instrument in the same position as FIG. 1 but now the instrument being in closed jaws function and with a partially cross sectional view of the near ending.

FIG. 4 is a cross-sectional view of FIG. 1 taken along line BB.

FIG. 5 is a cross-sectional view of FIG. 1 taken along line CC.

Figure 6:
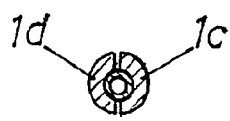
FIG. 6 is a cross-sectional view of FIG. 2 taken along line DD.

For better understanding, FIGS. 1, 2, 3, 4 and 5 were drawn on a 2:1 scale, and FIGS. 6, 7, 8 and 10 on a 3:1 scale.

DETAILED DESCRIPTION OF THE INVENTION

The simultaneous observation of all figures allows the description to be ordered getting a better understanding of the instrument structure and functioning, It is possible to see the second tube (tube 2) having the same diameter along its bigger length and an oblique opening on one of the endings, which associated with an elbowed segment 2a makes the 1f and 1g jaws pressing enhance its efficiency. On the opposite ending, the second tube presents the 2b and 2c rings which keep united with each other only by projections 2d and 2e. The inner diameter of ring 2b allows the sliding of the first tube (tube 1). FIG. 4 shows the inner opening of ring 2c; it is square to allow the member 3 of the handle to slide. This square opening presents a slot 2f cutting the ring on its whole height. FIG. 2 shows the first tube (tube 1) lodged into tube 2 being able to slide longitudinally and being longer than tube 2. The far ending of tube 1 presents needle 1a having elbow 1b. The forceps formed by arms 1c and 1d that are born on point 1e belong to tube 1, and from this point they distally project in a diverging way, having a regular section similar to a mid crown capable of covering the mid needle section (see FIGS. 6 and 7). This regular mid crown section keeps as far as the elbow on point 1b. Said elbow is accompanying the needle elbow, and from this elbow, the section is defined by a gradually increasing radio toward the final tip. The chord also increases but the arrow does not modify, reaching a last section as shown in FIG. 8. Jaws If and 1g are the forceps arm last segments and they present non-skid inner surfaces 1h shown in FIG. 11. An approximately 0.5-mm.-diameter hole is along the whole length of the longitudinal axis of tube 1. The near ending of tube 1 is fixedly inserted into the inner diameter of a handle. Member 3 of the handle has a square outer section crossing the inner opening of ring 2c and this member presents a threaded cylindrical segment 3b on one end, and, on the other end it presents a disc 3a having two plane faces which are a continuation of respective opposite faces in the square section. A hole extending along the member crosses the disc diametrically communicating the inner diameter of tube 1 with a tubular appendix 3c. A flex tube 5 whose free end has a cone for syringe 5a and its plug 5b is welded on the appendix. A rotative button with bidigital control 4 is mounted on threaded segment 3b of the handle This rotative button is a cylinder of annular section having a non skid outer surface and an inner diameter in its whole height threaded the same as the thread on segment 3b.

Radio transparent and non-resterilizable material can be used for making the complete instrument.

The final constructive stage of the instrument comprises the assembly in this way:

1-Rotative button 4 is threaded on segment 3b of handle.

2-The foresaid assembly is mounted in tube 2 exerting pressure on member 3 of the handle against slot 2f for locating it in the central square section, being careful that the plane of disc 3a and the one containing projections 2d and 2e are the same.

3-The near ending of tube 1 is inserted into the far ending of tube 2 so as to penetrate into the handle until the end. While last segment 2a of tube 2 is slid toward 1g and 1f we check that it is in mating position with them, and so, keeping this relative position a permanent fastening is made between tube 1 and the handle employing the most suitable method (thermal fusion, contact cement etc.).

Being in closed jaw function, the instrument is introduced into the abdominal cavity through cannula 9, which together with its respective trocar have been placed in a selected point of the abdominal wall. When the instrument is in the abdominal cavity, the rotational movement of button 4 according to the turn sense makes tube 2 either go up or go down and the jaws move away or come together respectively. The cannula and its trocar are conventional and they are not part of the present invention but it is necessary to point out that the cannula material and thickness must be suitable for getting enough both elasticity and plasticity allowing the elbowed tip of the instrument to slide such as shown in the GG and HH sections of FIG. 10. Looking at sections GG and HH, it is possible to infer that the bigger perimeter of the closed jaw section does not have to be bigger than the perimeter of the second tube outer diameter.

Figure 11:
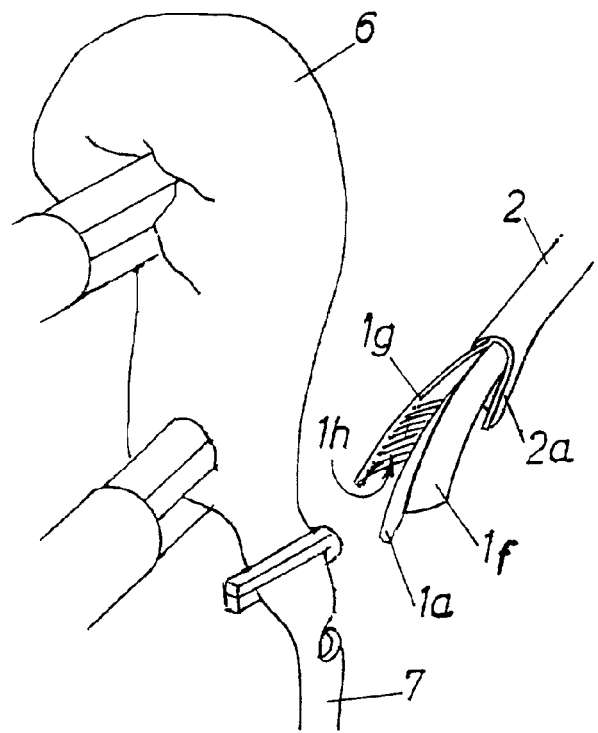
FIGS. 11, 12 and 13 show the needle in a sequence of images going from the needle near the cystic duct opening to the insertion and pressing of it, thereby the instrument is in suitable condition for the radiopaque medium to be injected.
Figure 12:
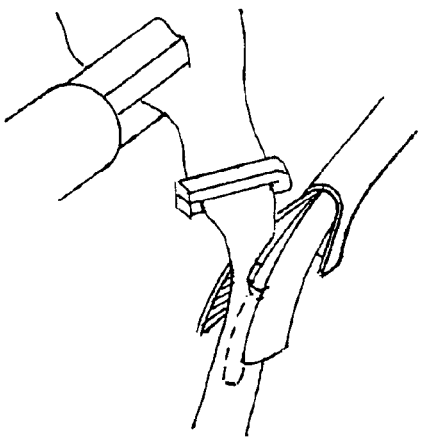
Figure 13:
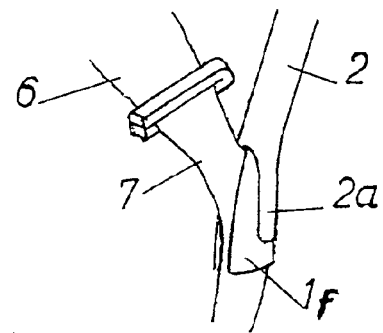
Figure 14:
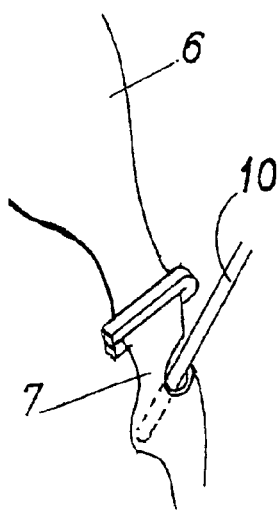
FIG. 14 shows a cystic duct being cannulated by a straight needle and the risk of the duct being opened by it.

FIGS. 11, 12 and 13 show gallbladder 6 and cystic duct 7 and comprise a sequence of images from the needle tip approaching the cystic duct opening to the cystic duct cannulating by the needle, and the pressing of them. These figs. also allow the understanding of the advantages of the elbowed needle: the elbow makes the needle axis and the cystic duct axis to be almost parallel with each other, lowering the risk for injuring the cystic wall on the opposite point of the way in. FIG. 14 shows the cystic injury risk employing a totally straight needle 10.

Figure 7:
FIG. 7 is a cross-sectional view of FIG. 2 taken along line EE.
Figure 8:
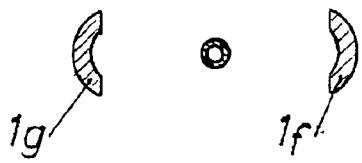
FIG. 8 is a cross-sectional view of FIG. 2 taken along line FF.
Figure 10:
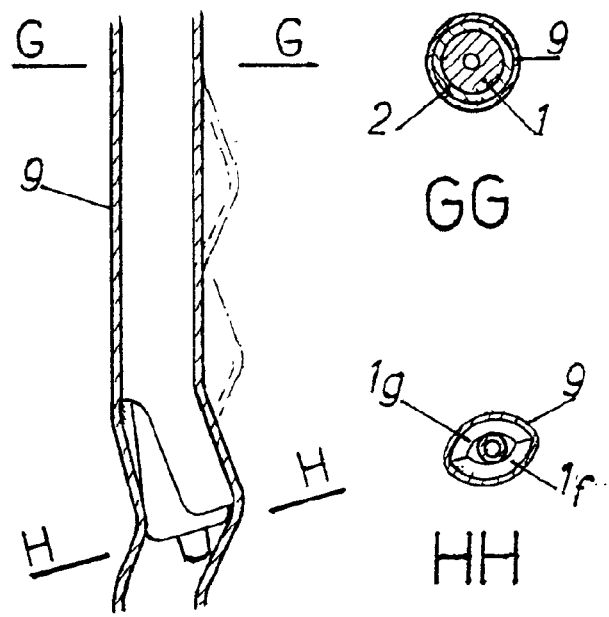
FIG. 10 is a longitudinal cross-section of the cannula containing the instrument far ending and showing the wall cannula changes happening during successive steps of the far end sliding in dashed lines. It also shows both cross section GG taken along the plane, which cuts the first tube body, and cross section HH taken along the plane, which cuts the instrument tip.
Figure 9:
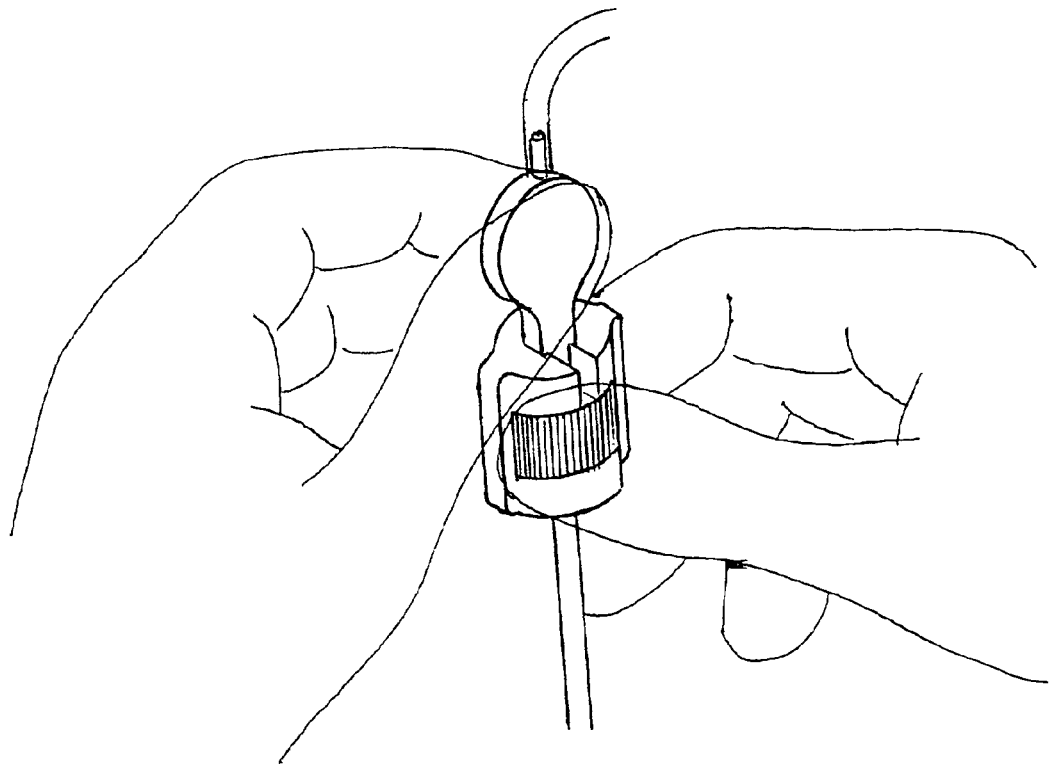
FIG. 9 shows the manual driving of the digital button in a three-dimensional way.
Figure 15:
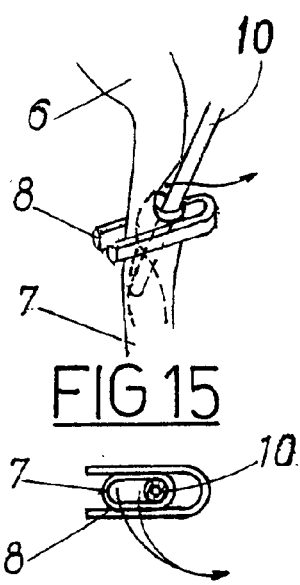
FIG. 15 shows a cystic duct cannulated by the needle and its fastening by a clip.
Figure 16:
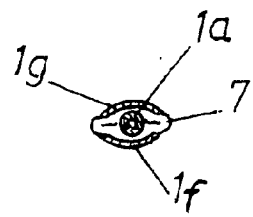
FIG. 16 is a cross section view of FIG. 15 taken along a plane passing on the clip border.
Figure 17:
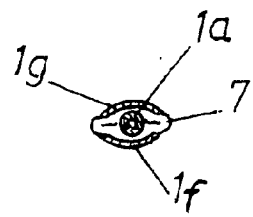
FIG. 17 is a cross section view of FIG. 13 along a plane that cuts the jaws near their far endings.

FIGS. 6, 7 and 8 show forceps arms 1d and 1c, and their jaws 1g and 1f having a curved section accompanying the needle section and therefore also the cystic duct section when the needle is inserted into it. This fact is important for avoiding the injected liquid to escape outside the duct even when the needle should have been loosely introduced into the duct. This is a great advantage in comparison with the employing of a clip and it is easy to understand looking at FIGS. 15 and 16: when clip 8 is mounted, its arms keep parallel with each other and the cystic wall is only partially flattened and then through the cystic opening used for getting needle 10 into the cystic duct, an outward communication channel is formed where the contrast liquid may flow, following the dashed lines and the arrows. On the contrary fact the jaws of the present instrument make a closing according to FIG. 17 and obviously such escape can not happen.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An instrument for performing surgical cholangiographys of the kind which require cystic duct cannulating for injecting a radiopaque liquid comprising:

a first tube having a distal ending forming an instrument needle with an outer diameter which is smaller than the remaining outer diameter of the first tube, both diameters being concentric and having a common axis, diametrically opposed bearing points of respective and symmetric projections of said first tube placed at sides of a location of needle birth, the projections defining arms of a forceps, having half-crown sections, and having concavities which confront each other, the needle being centered between said projections, the projections extending from and remaining at both sides of the needle, the projections being contained in a common plane with said needle and advancing in a divergent way so that the needle remains centered on the common axis and each projection axis determines, with said common axis, an approximately 15 degree angle with a vertex located on a respective one of said bearing points, said needle and said projections having an elbow followed by last segments such that an approximately 15 degree angle between said last segments and said common plane is formed, the approximately 15 degree angles all being contained in respective planes which are at right angles with respect to said common plane so that, if both projections are pressed toward each other, they turn around respective bearing points and are able to contact each other, the needle remaining placed between the projections so that the needle axis becomes the central axis of both projections along their whole lengths, the last segment of the needle having a slight olive form, the last segments of both projections having a half crown initial section, the last segment sections not changing in orientation but gradually increasing both in chords and radii up to respective tips so as to reach maximums, said last segments of said projections defining forceps jaws which elastically recover the approximately 15° angle if pressing is released after said forceps jaws have been pressed into contact with each other, the first tube having a hollow inner diameter along its whole length and being centered on said common axis;

a tubular member which has a square outer section but, on a small segment on its distal ending, also has a circular shape and is threaded, a proximal ending of said first tube being fixedly lodged in an inner diameter of said tubular member;

an inner threaded annular section cylinder mounted on said tubular member to define a rotative bidigital control, said tubular member, on a proximal ending, becoming a disc with two plane faces, which are circularly expanded continuations of two opposite faces of said square outer section and, together with said tubular member, form a handle, a hole centered on said common axis crossing said disc diametrically and, following along said tubular member, reaching the first tube, the hole, from the opposite end, continuing through a tubular appendix to said disc; and a second tube, having inner and outer diameters, said first tube slidably mounted in said second tube, said second tube ending near the needle with an oblique opening and a last segment bent at an approximately 15 degree angle with respect to said common axis, said angle of the last segment being contained in the same plane containing the elbow and mating with a convex angle which is determined by said forceps jaws when said second tube is wholly slid to make the jaws contact each other, the second tube, at an end opposite the ending near the needle, having an outer diameter bigger along a ring, which has two diametrically opposite projections parallel with each other and with said common axis and extended a length corresponding to the length of said inner threaded annular section cylinder so as to reach and join another ring with an inner section which is square so as to mate with said square outer section, one side of the inner section which is square being open outward along its whole height.

2. The instrument according to claim 1, wherein said forceps jaws are driven by a rotative bidigital control.

3. The instrument according to claim 1, wherein when said forceps jaws are pressed to contact with each other and released, they recover their previous positions because of their elasticity.

4. The instrument according to claim 1, wherein the forceps jaws and the needle form a single piece.

5. The instrument according to claim 1, wherein the jaws providing concavities, confronting with the convexity that is defined by the needle diameter, have non skid surfaces for pressing.

6. The instrument according to claim 1, wherein a bigger outer perimeter of a section which both closed jaws define is no bigger than the perimeter of the second tube outer diameter.

7. The instrument according to claim 1, wherein the tip of the second tube which operates on the jaw has both an oblique opening and an elbowed last segment mating with the angle of the jaws when they are closed.

8. The instrument according to claim 1, wherein the needle has an elbowed last segment at approximately a 15-degree angle and with said slight olive form.

9. The instrument according to claim 1 wherein said ring with said square inner section has a slot crossing at right angles with respect to one of the square sides, the slot having a width less than that of the side of the square outer section of the tubular member but being elastically yieldable for surpassing the dimension of said side.

* * * * *